United States Patent [19]

Holman et al.

[11] 4,201,643
[45] May 6, 1980

[54] ANALYTICAL APPARATUS

[75] Inventors: David J. Holman, Blandford Forum; Howard James, Dorchester, both of England

[73] Assignee: United Kingdom Atomic Energy Authority, London, England

[21] Appl. No.: 891,454

[22] Filed: Mar. 29, 1978

Related U.S. Application Data

[60] Continuation of Ser. No. 707,078, Jul. 20, 1976, abandoned, which is a division of Ser. No. 583,900, Jun. 5, 1975, Pat. No. 4,025,308.

[30] Foreign Application Priority Data

Jun. 7, 1974 [GB] United Kingdom ............... 25458/74

[51] Int. Cl.² ............................................. B01D 13/02
[52] U.S. Cl. ................................. 204/180 R; 204/151
[58] Field of Search .................... 204/151, 180 P, 301, 204/149, 296, 180 R; 18/53; 264/317

[56] References Cited

U.S. PATENT DOCUMENTS

| | | | |
|---|---|---|---|
| 2,155,016 | 4/1939 | Kershaw | 18/53 |
| 2,341,356 | 2/1944 | Briggs | 204/151 |
| 3,116,355 | 12/1963 | Oswin | 264/317 |
| 3,623,969 | 11/1971 | Hushihara | 204/151 X |
| 3,677,923 | 7/1972 | Bier | 204/180 R X |
| 3,751,356 | 8/1973 | Takeya et al. | 204/301 X |
| 3,930,979 | 1/1976 | Vallance | 204/151 X |
| 3,969,207 | 7/1976 | Kerti et al. | 204/151 X |
| 4,048,044 | 9/1977 | Erbl et al. | 204/151 X |

FOREIGN PATENT DOCUMENTS 1081046  8/1967  United Kingdom.

Primary Examiner—Arthur C. Prescott
Attorney, Agent, or Firm—Larson, Taylor and Hinds

[57] ABSTRACT

A method and apparatus for monitoring low concentrations of certain ions present in a flowing fluid is described in which an isokinetic sample is passed through an electro-separative cell wherein, under the influence of an applied electrical field microgram quantities of the ionic species are quantitatively transferred through a microporous filter membrane. The membrane has a pore size related to cell efficiency.

5 Claims, 3 Drawing Figures

4,201,643

ANALYTICAL APPARATUS

This is a continuation of application Ser. No. 707,078, filed July 20, 1976, now abandoned, which in turn is a divisional application of Ser. No. 583,900 filed June 5, 1975, U.S. Pat. No. 4,025,308.

BACKGROUND OF THE INVENTION

This invention relates to analytical apparatus and the methods for analytical monitoring of liquids, and further relates to the preparation of water in a condition free of ions of a certain selected species.

A requirement which frequently arises in relation to plant using or treating certain liquids is that the plant operator should know or have means for ascertaining the concentration of chemical species present in the liquid being treated or processed. There may be many reasons why the need for this information arises, for example the need for quality control of a particular product, or the need for checking the presence of corrosion-inducing species or the need for economy in the use of expensive additives to certain process liquids. Where the concentrations of interest fall below, or at the lower end of, the measuring range of conventional analytical instruments, difficulties arise in providing the plant operator with the data he needs and he remain unaware whether corrective action is necessary. One such difficulty arises in the monitoring of corrosion and stress corrosion cracking of stainless steel components by chloride species in high pressure boiler systems where it is important that any chlorides should be at a very low level. It is our experience that the chloride level in the feed water is already below the limit of detection by the on-stream colorimetric method and the requirement exists for monitoring even lower levels than are measurable by this means.

SUMMARY OF THE INVENTION

According to the present invention in one aspect an analytical apparatus for detecting the presence of, or measuring, low concentrations of ions of a selected species in solution in a liquid, includes an electroseparative cell having a compartment for containing a specimen liquid substantially devoid of the selected species and a sample compartment adapted to form part of a flowpath for a flowing isokinetic sample of the liquid, a microporous neutral membrane separating the compartments; an electrode in each compartment which is selectively energised to attract the said ions from the flowing sample into the compartment for containing the specimen and a means for measuring the concentration of the ion species of interest accumulated in the specimen compartment.

Preferably electrodes of different polarity are supported one in each compartment and the metal portions of the compartments ie the sample and specimen inlet and outlet ports, are earthed. The specimen liquid may be a static volume of liquid, which is drained periodically and the concentration of the species of interest present measured. Alternatively the compartment for the specimen liquid may be adapted to form part of a flow path for a stream of specimen liquid substantially devoid of the species of interest. Means are then provided for directing the specimen outlet flow through the measuring means.

It is of advantage to ensure that the specimen is made devoid of the species of interest by the same means as is employed to subsequently concentrate said species in the specimen and electroseparation has special merit in this respect. Hence the specimen, whether static or flowing is itself preferably the product of purification ie made free of the ions of the species of interest by electro-separation.

The apparatus finds particular application in monitoring boiler feed water for the presence of species in concentrations too low for conventional measurement yet liable to promote the onset of some deleterious condition, such as corrosion. According to this aspect the invention may comprise, in a steam boiler installation an analytical apparatus for monitoring the presernce of ions of said species which may be present in solution in the boiler feed water the apparatus comprising first and second similar electro-separative cells,—each cell having a sample compartment and a specimen compartment separated by a microporous membrane and electrodes of opposite polarity in respective compartment, means for flowing a sample of boiler feed water through the sample compartment of the first cell with the polarity of its electrodes arranged to attract species of interest through the micro-porous membrane into the adjacent specimen compartment, said adjacent compartment containing a static or flowing specimen of water made substantially devoid of said species by electro separative treatment in said second cell and means for analysing the concentrated species in the specimen compartment of the first cell. The source of said static or flowing specimen in the compartment of the first cell may be the condensate well of the steam plant associated with the steam boiler. In some cases the condensate may be passed directly to the first electroseparative cell and sample liquid may be recycled, after purification, eg by electrodialysis or other means, back to the specimen compartment of the first cell. The invention also resides in a method of monitoring a flowing liquid for the presence of ions of a selected species present in concentrations too low for routine measurement, the method residing in tapping an isokinetic sample from a flowing liquid, flowing the sample through a chamber bounded by one side of a porous membrane whilst maintaining an electrical potential on the other side of the porous membrane sufficient to effect transport of selected ions from the flowing liquid through the membrane into a volume of liquid initially substantially free of said ions whereby said ions become concentrated in the volume of liquid, continuing the isokinetic sample flow until a concentration of ions sufficient for measurment has been achieved and then measuring said concentration and relating that measurement to the total flow of liquid.

It will be understood by those skilled in the art that the above process may be employed for preparing blank water for analytical purposes.

DESCRIPTION OF THE DRAWINGS

In order that the invention may be better understood the analytical apparatus, applications and methods will now be explained with reference to the embodiments of the invention shown in the accompanying diagrammatic drawings in which.

Figure 1:
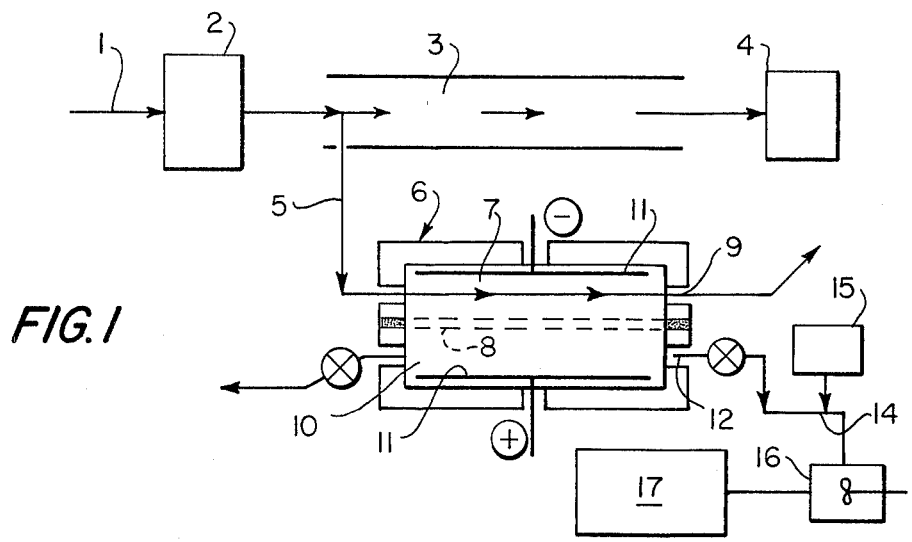
FIG. 1 shows an analytical apparatus for measuring low concentrations in a liquid

Referring firstly to FIG. 1, the reference 1 indicates a raw water supply line supplying water via a treatment plant 2 through duct 3 to a process plant 4. The requirement is to measure the presence of a certain ionisable specie (referred to herein as the specie(s) of interest) in the water, in concentrations below that easily measurable by conventional plant instruments. To this end, a tapping pipe 5 from the duct 3 leads an isokinetic sample flow to an electro-separative cell 6. The sample passes through one (cathode) compartment 7 in the cell bounded on one side by a microporous membrane 8 and thence, via outlet 9, to waste. The membrane 8 was a Millipore cellulose estor filter membrane with holes about 0.45 μm diameter supplied by the Millipore Co. UK. The membrane was not ion-selective. On the other side of the membrane 8, a second compartment 10 contains as anolyte a static volume of liqud from which the specie(s) of interest have been removed, eg by electrodialysis, so that it is substantially devoid of said specie(s), or as devoid as it may be made by electrodialysis.

Each compartment has a plate electrode 11 of platinum arranged to be energised by 100 volts dc supply in a sense to attract negative chloride ions from the sample flow through the membrane 8, which is porous, into the specimen volume in compartment 10. Once the latter contains a higher concentration of chloride ions, the content is drained via normally closed outlet 12 into pipe 14. The liquid is treated with reagent from a supply 15 and passed through a mixer 16. Having been mixed with a chloride reagent, the mixture is passed to a colorimeter 17 wherein the concentration of chloride species is measured. The chamber 10 is then recharged with a fresh volume of water devoid of the species of interest and the same cycle is repeated. Laboratory tests using radio-chlorine tracers have shown that the cell efficiency to be greater than 90% at a chloride concentration of $\mu g l^{-1}$ with a sample flow of 30 ml min$^{-1}$, the isokinetic sample flow rate for a nuclear boiler channel.

Figure 2:
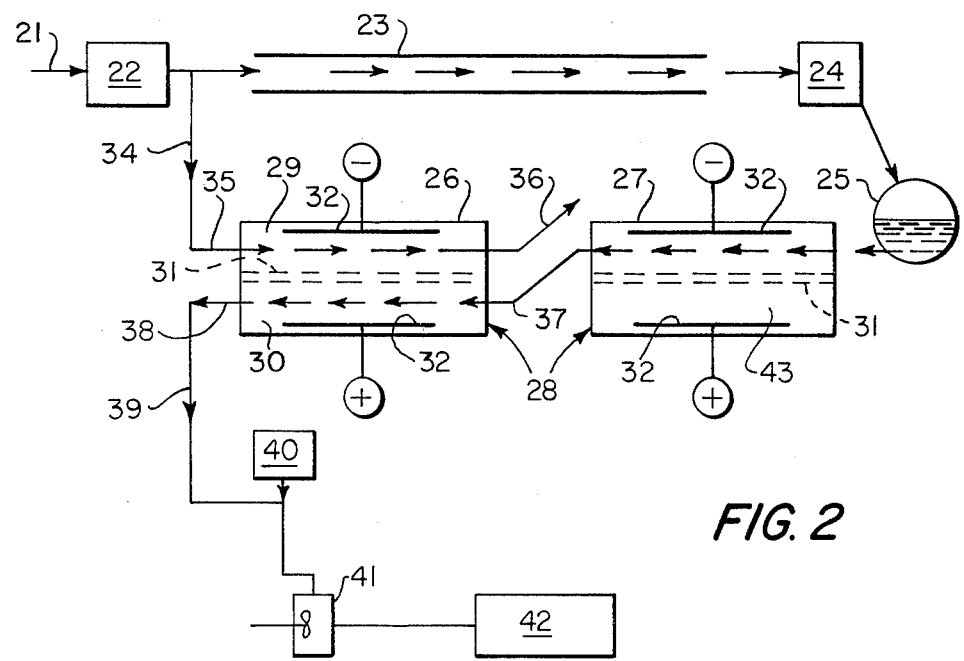
FIG. 2 shows a similar apparatus as applied to measure low concentrations of selected species in boiler feed water and FIG. 3 shows graphically the relationship between various pore sizes of the microporous membrane and chloride concentration efficiency; the pore sizes lying in the range 0.01 to 1.2 μm.

FIG. 2 shows a modified form of the apparatus in FIG. 1 as applied to analyse boiler feed water for chloride species which are known to be responsible for corrosion of the boiler internals.

So in FIG. 2, reference 21 indicates a water supply line leading to a water treatment plant 22, from which water preheated in feed heaters (not shown) is passed via main 23 to a steam boiler plant 24. Pertaining to the latter, a condensate well 25 is shown for reasons which will appear later.

In order to monitor the feed water for deleterious species such as, in this case chlorides, an analysing apparatus is provided. The latter comprises a pair of electrocialysis cells 26, 27 each of similar construction comprising a hollow body 28 divided into two compartments 29, 30 by a microporous membrane 31. Platinum sheet electrodes 32 are polarised in a sense chosen in cooperation with the selective nature of the solute to separate a given species, as will become apparent from the following description.

A tapping pipe 34 leads a sample flow into inlet 35 at one end of compartment 29 bounded by the membrane 31. The sample flow runs the length of the compartment 29 and allowed to run to waste from an outlet 36 at the other end of the compartment. Simultaneously, a flow of specimen water devoid of the species of interest is flowed in countercurrent to the sample flow into inlet 37 into the compartment 30 of cell 26 through the compartment 30 and out through outlet 38 into pipe 39. Flow through compartment 29 is arranged to be ten times the flow through compartment 30 in order that a ten fold concentration effect may be achieved. It will be understood that, for the analysis of chlorides, the electrode 32 in compartment 30 is given a positive potential relative to that in compartment 29 so that, with the microporous membrane 31 anion permeable, any chloride ions in the sample flow will be attracted into the stream of specimen water. This stream passes through pipe 39 where colorimeter reagent is added from a supply 40 with which the water is mixed in mixer 41 before entering colorimeter 42. A pen recorder records the amount of chloride present in the mixture.

The source of water devoid of the species of interest for supply to the compartment 37 is conveniently the condensate in the well 25 of the steam plant 24. The high purity condensate is first treated in the second electrodialysis cell 27 to remove said species before being passed to inlet 37. In cell 27 the polarities are such that any chloride ions present in the condensate are attracted through the membrane 31 therein into a static volume 43 of water (which is replaced when its chloride ion concentration becomes too high). The stream leaving the cell 27 is thus high purity water devoid of chlorides.

Although the emphasis in the foregoing has been on testing for chlorides the invention is equally applicable to the testing of liquids for phosphates, sulphates, nitrates etc care being taken to adjust the polarity of the electrodes and the porosity of the membrane where necessary.

The concentration of positive charged species (cations) is also possible; however, as the cations are discharged and deposited on the platinum electrode, in order of increasing negative potential, there would be a risk that some species (eg iron copper, nickel, etc) will plate out of solution.

The invention may be adapted for the concentration of alkali metals and alkaline earths (eg sodium potassium, calcium, magnesium etc).

The invention may also be adapted to provide a system for de-anionising water (or other liquid) for use when the negative ion content of the water is required to be low. Conversely, a static catholyte system could be employed to remove traces of positive ions from water flowing through the anode compartment.

The membranes employed in these cells may be ionselective, but, in current examples microporous, ie neutral membranes are used and these should be very thin as a precaution against the transported ions being held up in the pores of the membrane and never reaching the specimen compartment. For this reason membranes of between 7–200 μm; typically about 100 μm thick membranes in cellulore acetate or about 10 μm thick in polycarbonate are preferred.

The term electroseparative has been employed because electrodialysis implies the use of ion-selective membranes and the invention is not necessarily limited in this respect. It is to be noted that electroseparative processes are very suitable for the important monitoring liquid flow systems described because only flow systems are likely to avoid subsequent contamination of chloride/sulphate at the very low concentration levels present in the input sample. There are very low levels for example in some boiler feed water which has already been treated eg less than 0.5 microgram per liter.

Figure 3:
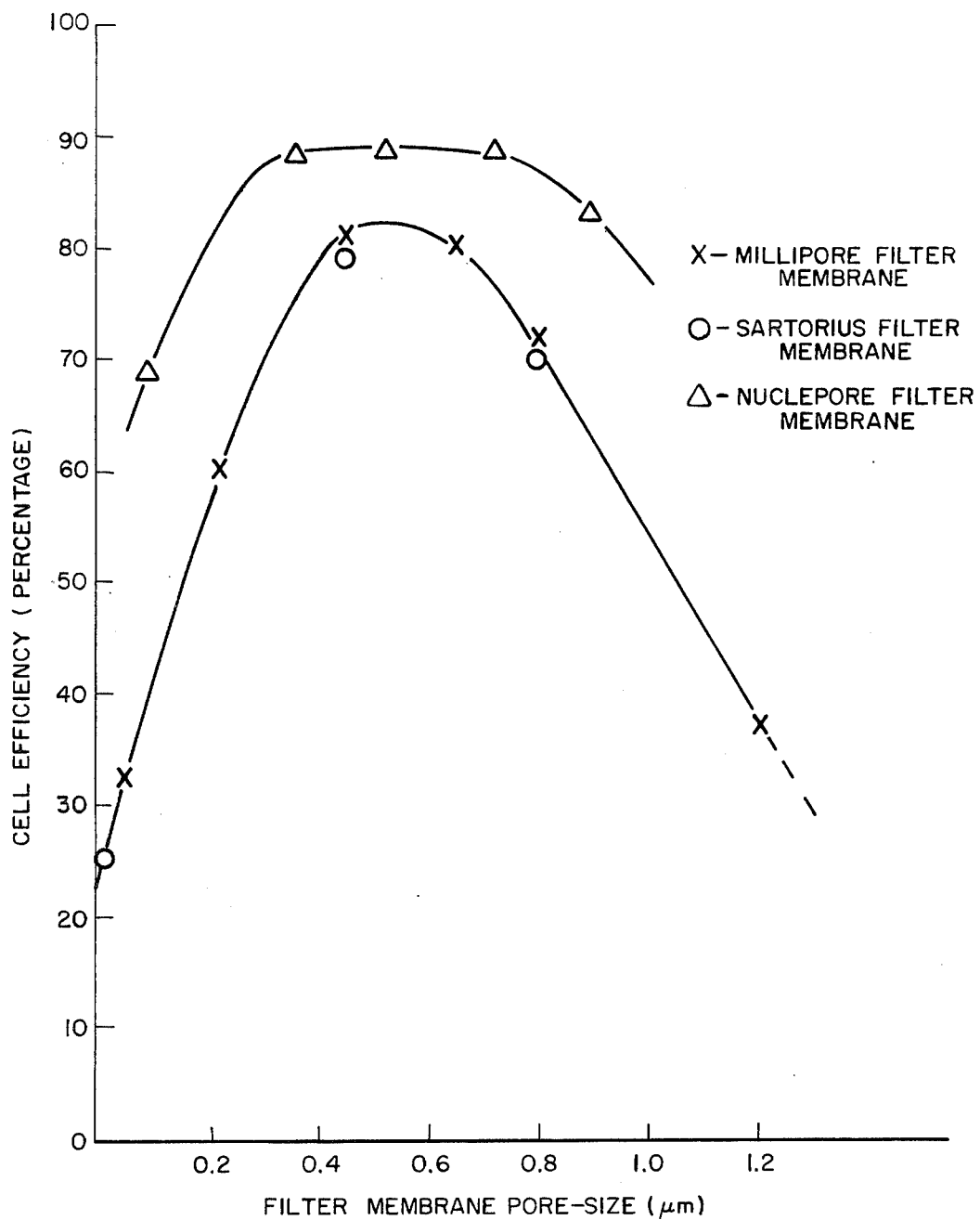

The results of a series of comparative tests on different microporous filters and their effect on efficiency of concentration is shown in FIG. 3. These show that the pore size of the membrane is critical of a high cell efficiency is to be obtained. The optimum range of pore size is very narrow lying between about 0.4 and 1.0 μm. The specification of the membranes was as follows:

| Microporous Filter | Material | Membrane Thickness |
|---|---|---|
| 'Millipore' | Mixed esters of cellulose | ca 150 μm |
| 'Sartorius' | Cellulose nitrate | ca 90–140 μm |
| 'Nuclepore' | Polycarbonate film | ca 10 μm |

In a series of tests designed to obtain the optimum pore size membrane for chloride migration, separate five-liter volumes of water were spiked with $^{36}Cl$ tracer and standard chloride to a chloride concentration of 10 $\mu g l^{-1}$. The solutions were then passed through the cathode compartment at a flow rate of 28 ml min$^{-1}$ with an applied potential of 100 V dc across the cell. Chlorine-36 concentrated in the anolyte was determined, for calculation of cell retention efficiencies for individual membranes.

A Carlson-Ford Cox depth filter of glass/asbestos fibre (Cox M-780) was also tried but these relatively thick membranes were found to absorb the $^{36}Cl$ tracer and the cell retention efficiencies of chloride ions were very low in comparison with the thinner membranes.

What we claim is:

1. A method of reducing the amount of residual chloride ions in water after said water has previously been treated to remove the bulk of said ions, the method comprising,
   (a) passing said treated water through a compartment of an electrolytic cell;
   (b) presenting said treated water within the cell to one face of a porous non-ion selective membrane comprising a cellulose ester having pores of about 0.45 micrometers diameter and a thickness of about 150 micrometers to inhibit retention of said chloride ions in said pores so that to a substantial extent chloride ions can pass through said pores;
   (c) exposing the other face of the porous membrane to water substantially devoid of said residual chloride ions, and
   (d) simultaneously polarising the elctrolytic cell with a direct current supply of about 100 volts in a manner to attract anions and thereby the chloride ions from the treated water through the pores of the membrane and into the water substantially devoid of said chloride ions.

2. A method of reducing the amount of residual chloride ions in water after said water has previously been treated to remove the bulk of said ions, the method comprising,
   (a) passing said treated water through a compartment of an electrolytic cell;
   (b) presenting said treated water within the cell to one face of a porous non-ion selective membrane comprising cellulose nitrate having pores sized between 0.4 to 0.6 micrometers diameter and a thickness of between 90 to 140 micrometers to inhibit retention of said chloride ions in said pores so that to a substantial extent chloride ions can pass through said pores;
   (c) exposing the other face of the porous membrane to water substantially devoid of said residual chloride ions, and
   (d) simultaneously polarising the electrolytic cell with a direct current supply of about 100 volts in a manner to attract anions and thereby the chloride ions from the treated water through the pores of the membrane and into the water substantially devoid of said chloride ions.

3. A method of reducing the amount of residual chloride ions in water after said water has previously been treated to remove the bulk of said ions, the method comprising,
   (a) passing said treated water through a compartment of an electrolytic cell;
   (b) presenting said treated water within the cell to one face of a porous non-ion selective membrane comprising a polycarbonate film having pores sized between 0.4 to 1.0 micrometers diameter and a thickness of about 10 micrometers to inhibit retention of said chloride ions in said pores so that to a substantial extent chloride ions can pass through said pores;
   (c) exposing the other face of the porous membrane to water substantially devoid of said residual chloride ions, and
   (d) simultaneously polarising the electrolytic cell with a direct current supply of about 100 volts in a manner to attract anions and thereby the chloride ions from the treated water through the pores of the membrane and into the water substantially devoid of said chloride ions.

4. A method of reducing the amount of residual chloride and sulphate ions in water after said water has previously been treated to remove the bulk of said ions, the method comprising,
   (a) passing said treated water through a compartment of an electrolytic cell;
   (b) presenting said treated water within the cell to one face of a porous non-ion selective membrane, the membrane having pores sized in the range of about 0.2 to 1.0 micrometers diameter and a thinness so chosen as to inhibit retention of said chloride and sulphate ions in said pores so that to a substantial extent chloride and sulphate ions can pass through said pores;
   (c) exposing the other face of the porous membrane to water substantially devoid of said residual chloride and sulphate ions, and
   (d) simultaneously polarising the electrolytic cell with a direct current supply of the order of 100 volts in a manner to attract anions and thereby the chloride and sulphate ions from the treated water through the pores of the membrane and into the water substantially devoid of said chloride and sulphate ions.

5. A method of reducing the amount of residual chloride and sulphate ions in water in an electrolytic cell after said water has previously been treated to remove the bulk of said ions, the method comprising:
   (a) passing a first portion of the treated water through one of two oppositely polarised electrolytic cells connected together in series relationship, each cell comprising a first compartment, a second compartment, and a porous non-ion selective membrane which is arranged to separate the compartments and have pores sized in the range of about 0.2 to 1.0 micrometer diameter and a thinness so chosen as to inhibit retention of said chloride and sulphate ions in said pores so that to a substantial extent chloride and sulphate ions can pass through said pores;

(b) passing a second portion of the treated water through both said cells but at a lower rate of flow than said first portion of the treated water, said first portion passing through the compartment of said one cell, and said second portion passing through the first compartment of the other cell and the second compartment of said one cell, and said other cell containing water substantially devoid of said chloride and sulphate ions in the second compartment thereof, and (c) simultaneously polarising the electrolytic cells with a direct current supply of the order of 100 volts in a manner to attract anions and thereby the chloride and sulphate ions from the first compartment to the second compartment of each cell through the pores of said membrane, thereby to produce from said first portion of treated water a water substantially deficient in said ions.

* * * * *